United States Patent
Imayama et al.

(10) Patent No.: US 11,250,183 B2
(45) Date of Patent: Feb. 15, 2022

(54) SIMULATION METHOD AND SIMULATION APPARATUS

(71) Applicant: SUMITOMO HEAVY INDUSTRIES, LTD., Tokyo (JP)

(72) Inventors: Shintaro Imayama, Kanagawa (JP); Ryouta Hirose, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 636 days.

(21) Appl. No.: 16/042,156

(22) Filed: Jul. 23, 2018

(65) Prior Publication Data
US 2019/0065643 A1 Feb. 28, 2019

(30) Foreign Application Priority Data
Aug. 30, 2017 (JP) .............................. JP2017-165035

(51) Int. Cl.
*G06F 30/20* (2020.01)
*G16C 10/00* (2019.01)
*G16C 99/00* (2019.01)

(52) U.S. Cl.
CPC ............. *G06F 30/20* (2020.01); *G16C 10/00* (2019.02); *G16C 99/00* (2019.02)

(58) Field of Classification Search
CPC .......... G06F 30/20; G16C 10/00; G16C 99/00
USPC .......................................................... 703/9
See application file for complete search history.

(56) References Cited

U.S. PATENT DOCUMENTS

| 10,549,453 | B2 * | 2/2020 | Tomiyama | B29B 7/48 |
| 2013/0018641 | A1 * | 1/2013 | Prisco | G06F 30/20 703/9 |
| 2015/0186572 | A1 * | 7/2015 | Ohnishi | G06F 17/18 703/2 |
| 2016/0342772 | A1 | 11/2016 | Ichishima | |

FOREIGN PATENT DOCUMENTS

| JP | 2016-218767 A | 12/2016 |
| JP | 2017-004103 A | 1/2017 |

OTHER PUBLICATIONS

C.F. Vardeman et al: "The Langevin Hull: Constant Pressure and Temperature Dynamics for Nonperiodic Systems", Journal of Chemical Theory and Computation, vol. 7, No. 4, pp. 834-842 (2011), XP055531505 (hereinafter 'Vardeman') (Year: 2011).*

(Continued)

*Primary Examiner* — Brian S Cook
*Assistant Examiner* — John E Johansen
(74) *Attorney, Agent, or Firm* — Michael Best & Friedrich LLP

(57) ABSTRACT

A flow field having an inflow/outflow interface is set as an analysis region, a fluid in the flow field is handled as an aggregate of a plurality of particles, and simulation is performed by using a molecular dynamics method. Here, a simulation method includes process of maintaining a temperature and a pressure in a heat bath at target values by compensating for changes in the temperature and the pressure in the heat bath with the passage of time in an analysis model in which the heat bath is connected to the inflow/outflow interface of the analysis region, and a particle is allowed to move between the heat bath and the analysis region.

2 Claims, 8 Drawing Sheets

(56) References Cited

OTHER PUBLICATIONS

C.F. Vardeman et al., "The Langevin Hull: Constant Pressure and Temperature Dynamics for Nonperiodic Systems," Journal of Chemical Theory and Computation, vol. 7, No. 4, XP055521505, ISSN: 1549-9618, DOI: 10.1021ct100670m, pp. 834-842, Apr. 12, 2011.
Search Report issued in European Patent Application No. 18183836.8, dated Jan. 2, 2019.
Office Action issued in European Patent Application No. 18183836.8, dated Jan. 25, 2019.

* cited by examiner

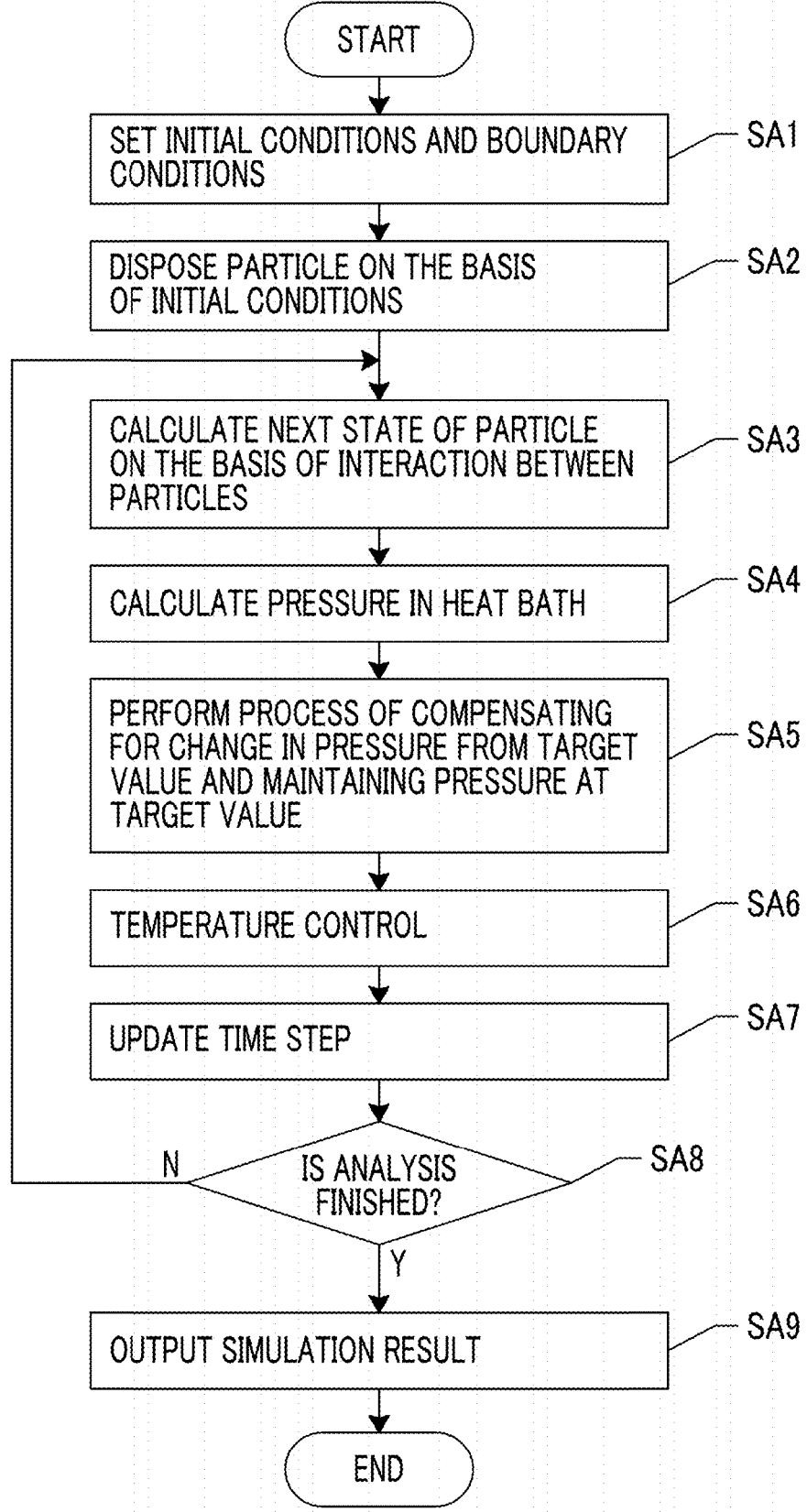

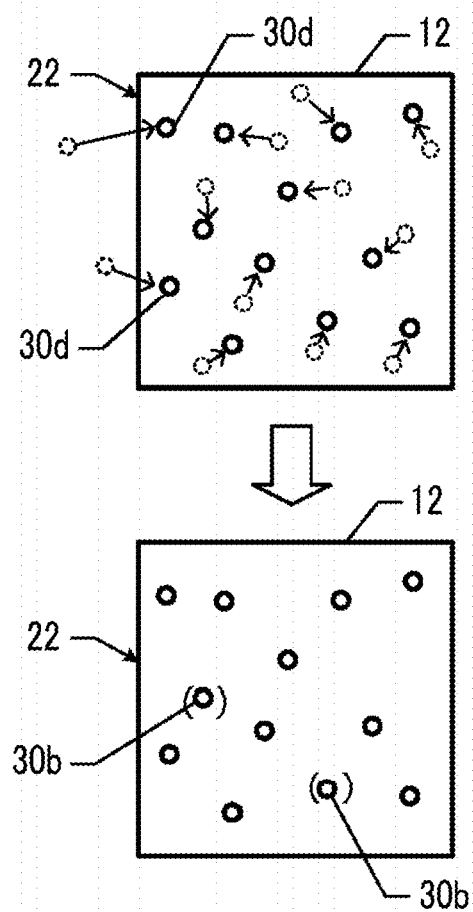

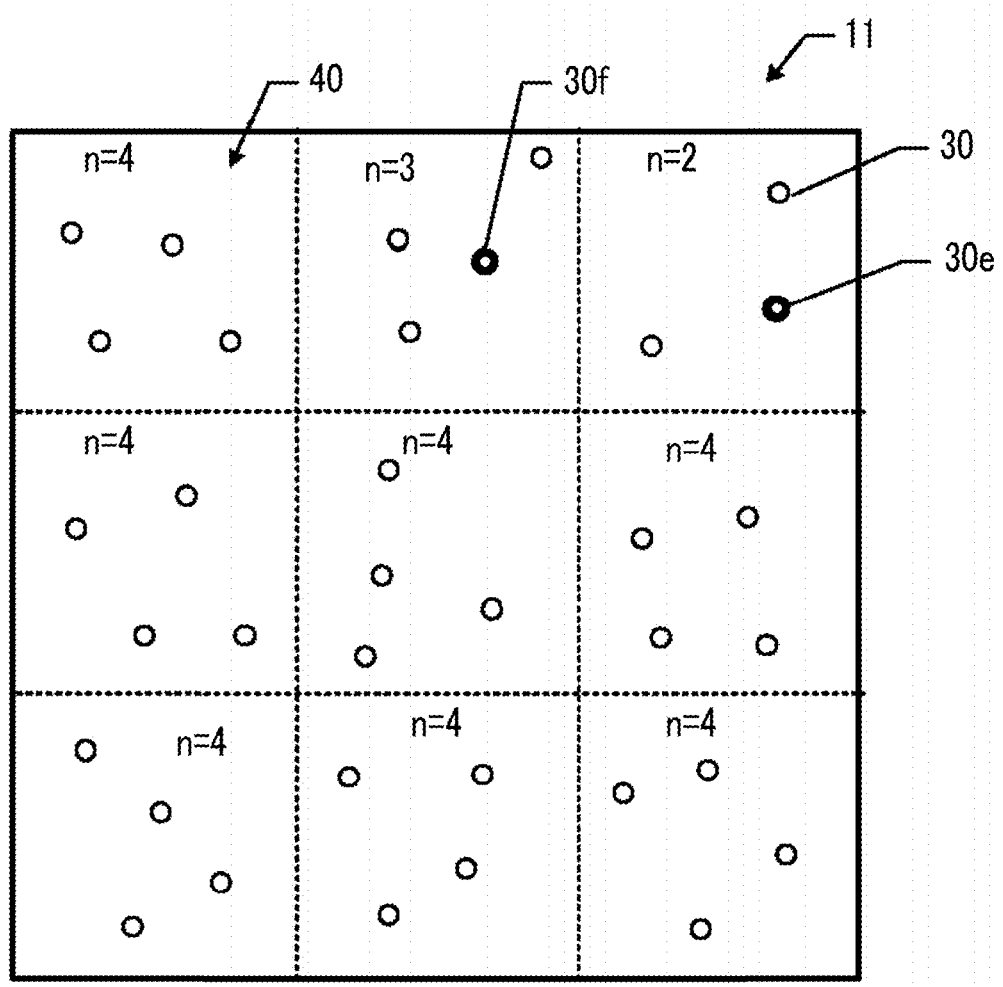

EMBODIMENT (PRESENCE OF PRESSURE CONTROL)

COMPARATIVE EXAMPLE (ABSENCE OF PRESSURE CONTROL)

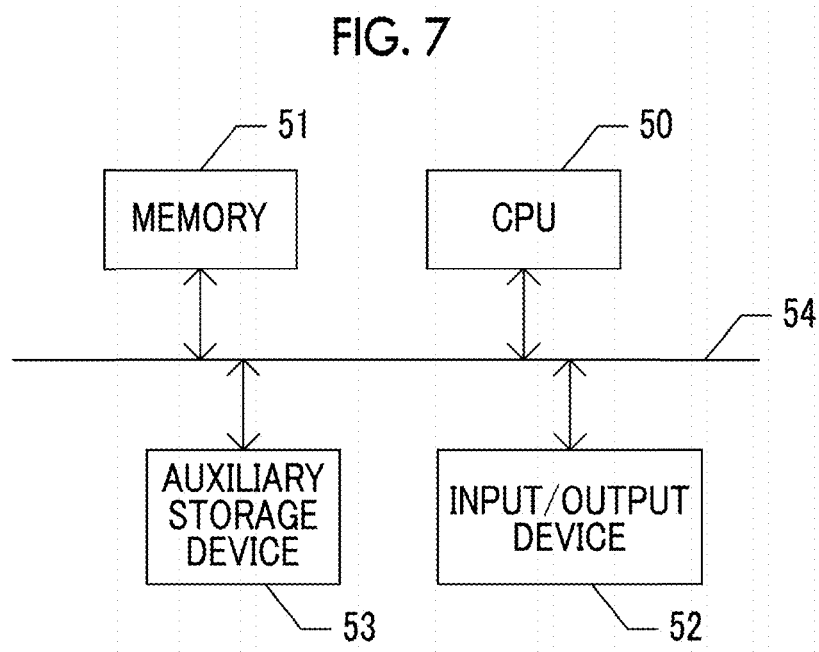

SIMULATION METHOD AND SIMULATION APPARATUS

RELATED APPLICATIONS

Priority is claimed to Japanese Patent Application No. 2017-165035, filed Aug. 30, 2017, the entire content of which is incorporated herein by reference.

BACKGROUND

Technical Field

A certain embodiment of the present invention relates to a simulation method and a simulation apparatus using a molecular dynamics method or a renormalized molecular dynamics method.

Description of Related Art

In a case where the temperature of steam decreases at a low pressure stage of a steam turbine, condensation occurs, and thus water droplets are generated. The water droplets collide with a rotor blade, and thus erosion occurs. In order to suppress the erosion, it is important to understand behaviors of steam and water droplets in the steam turbine. In the related art, in simulation analysis for a flow field of a fluid such as steam, the fluid is handled as a continuum. In such simulation analysis, it is hard to understand a detailed behavior of a flow field accompanied by a phase change from a gas to a liquid.

A technique has been proposed in which a behavior of a fluid is analyzed by performing simulation analysis according to a molecular dynamics method or a renormalized molecular dynamics method.

SUMMARY

In simulation analysis of the related art using a molecular dynamics method, it is hard to handle a system accompanied by inflow and outflow of a fluid. It is desirable to provide a simulation method and a simulation apparatus analyzing a system accompanied by inflow and outflow of a fluid by using a molecular dynamics method.

According to an aspect of the present invention, there is provided a simulation method in which a flow field having an inflow/outflow interface is set as an analysis region, a fluid in the flow field is handled as an aggregate of a plurality of particles, and simulation is performed by using a molecular dynamics method, the simulation method including: performing a process of maintaining a temperature and a pressure in a heat bath at target values by compensating for changes in the temperature and the pressure in the heat bath with the passage of time in an analysis model in which the heat bath is connected to the inflow/outflow interface of the analysis region, and a particle is allowed to move between the heat bath and the analysis region.

According to another aspect of the present invention, there is provided a simulation apparatus including: an input/output device; and a processing device that sets a flow field having an inflow/outflow interface as an analysis region, handles a fluid in the flow field as an aggregate of a plurality of particles, and analyzes a behavior of a particle by using a molecular dynamics method, in which the processing device acquires a target value of a temperature, a target value of a pressure, and an initial condition for the inflow/outflow interface of the analysis region from the input/output device, maintains a temperature and a pressure in a heat bath at target values by compensating for changes in the temperature and the pressure in the heat bath with the passage of time in an analysis model in which the heat bath is connected to the inflow/outflow interface of the analysis region, and a particle is allowed to move between the heat bath and the analysis region, and analyzes behaviors of particles in the analysis region and the heat bath by using the molecular dynamics method, and outputs an analysis result from the input/output device.

Since a heat bath is connected to an inflow/outflow interface of an analysis region, and a temperature and a pressure in the heat bath are maintained at target values, it is possible to control a temperature and a pressure at the inflow/outflow interface and thus to perform analysis.

BRIEF DESCRIPTION OF THE DRAWINGS

FIG. 2 is a flowchart illustrating a simulation method according to the embodiment.

FIG. 3C is a schematic diagram illustrating a state in which particles are removed in a case where the number dN is negative.

FIG. 4 is a schematic diagram illustrating a first heat bath for explaining the present modification example.

FIG. 7 is a block diagram illustrating a simulation apparatus according to the embodiment.

DETAILED DESCRIPTION

Figure 1:
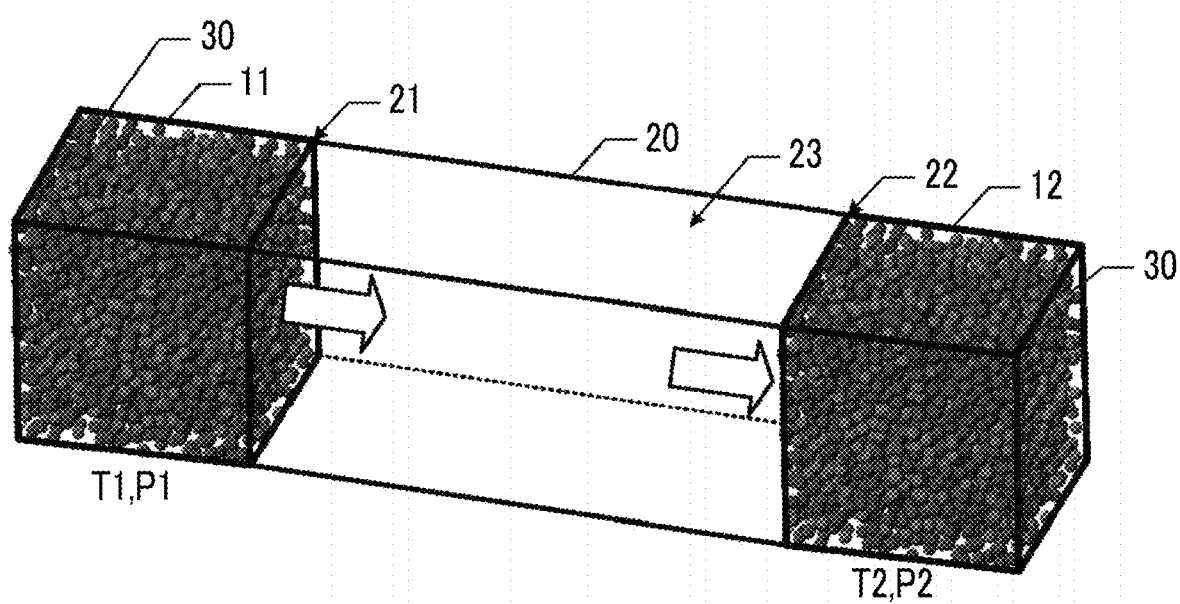
FIG. 1 is a schematic diagram illustrating an analysis model which is an analysis target in a simulation method according to an embodiment.

With reference to FIGS. 1 to 3, a description will be made of a simulation method according to an embodiment.

FIG. 1 is a schematic diagram illustrating an example of an analysis model which is an analysis target in the simulation method according to the embodiment. For example, an analysis region 20 having wall surfaces 23 and a pair of inflow/outflow interfaces 21 and 22 is defined. A flow field is formed in which a fluid, for example, water vapor flows into the analysis region 20 from one inflow/outflow interface 21, and the water vapor flows to the outside from the other inflow/outflow interface 22. This fluid is expressed by an aggregate of a plurality of particles, behaviors of the particles are analyzed by using a molecular dynamics method, and thus analysis of the flow field in the analysis region 20 is analyzed. As boundary conditions, a temperature T1 and a pressure P1 atone inflow/outflow interface 21 and a temperature T2 and a pressure P2 at the other inflow/outflow interface 22 are preferably controlled to have any values.

An analysis model is defined in which a first heat bath 11 and a second heat bath 12 are connected to the analysis region 20 via the inflow/outflow interfaces 21 and 22, respectively. Each of the first heat bath 11 and the second heat bath 12 is formed of, for example, a rectangular parallelepiped, and a particle 30 flow through surfaces in contact with the inflow/outflow interfaces 21 and 22. As mentioned above, the particle 30 is allowed to move between the first heat bath 11 and the second heat bath 12, and the analysis region 20. Reflectance boundary conditions are applied to other five surfaces of each of the first heat bath 11 and the second heat bath 12. The particle 30 which comes into contact with a reflectance boundary is reflected with a velocity component in a surface normal direction opposite to a direction when coming into contact. For example, a cyclic boundary condition or a reflectance boundary condition is applied to a wall surface 23 of the analysis region 20. If a pressure in the first heat bath 11 is set to be higher than a pressure in the second heat bath 12, a flow field directed from the inflow/outflow interface 21 to the inflow/outflow interface 22 is formed in the analysis region 20.

In a case where the analysis model illustrated in FIG. 1 is analyzed according to a typical molecular dynamics method, the particles 30 in the first heat bath 11 connected to the inflow/outflow interface 21 on the upstream side of the flow field flow into the analysis region 20, and are thus reduced with the passage of time. Conversely, the particles 30 in the second heat bath 12 connected to the inflow/outflow interface 22 on the downstream side of the flow field flow into the second heat bath 12 from the analysis region 20, and thus increase with the passage of time. Due to the change in the number of particles 30, the pressure in the first heat bath 11 is reduced with the passage of time, and the pressure in the second heat bath 12 increases with the passage of time. Thus, the pressure in each of the first heat bath 11 and the second heat bath 12 cannot be maintained at a constant target value. In the embodiment described below, a process of maintaining the pressure in each of the first heat bath 11 and the second heat bath 12 at a constant target value is performed.

FIG. 2 is a flowchart illustrating the simulation method according to the embodiment. First, initial conditions and boundary conditions for simulation are set (step SA1). The initial conditions include, for example, the number of particles, the mass of the particle 30, and positions and velocities of the plurality of particles 30. The boundary conditions include temperatures and pressures at the inflow/outflow interfaces 21 and 22 (FIG. 1). The temperatures and the pressures set in the boundary conditions are assumed to be target values of temperatures and pressures. Next, a plurality of particles 30 are disposed in the analysis region 20, the first heat bath 11, and the second heat bath 12 on the basis of the initial conditions (step SA2).

A motion equation is solved on the basis of interaction between the particles 30, and thus the next state of the particle 30 is calculated (step SA3). Specifically, a position and a velocity of the particle 30 after one time step are calculated. For example, a Lennard-Jones potential may be used as interaction between the particles 30.

The pressures in the first heat bath 11 and the second heat bath 12 are calculated on the basis of the next state of the particle 30 in the first heat bath 11 and the second heat bath 12 (step SA4). The pressures in the first heat bath 11 and the second heat bath 12 may be computed by using, for example, the virial theorem.

A process of maintaining the pressures P1 and P2 at the target values by compensating for variations from the target values of the pressures P1 and P2 in the next state in the first heat bath 11 and the second heat bath 12 calculated in step SA4 is performed (step SA5). Hereinafter, the process of maintaining a pressure at a target value will be referred to as pressure control. Details of the process will be described later with reference to FIGS. 3A to 3C.

Next, temperature control for maintaining the temperatures T1 and T2 in the first heat bath 11 and the second heat bath 12 at temperature target values is performed (step SA6). For example, a velocity scaling method may be used for the temperature control.

The pressure control and the temperature control are performed, and then a time step is updated (step SA7). Specifically, a state of the particle 30 obtained after performing the pressure control and the temperature control on the next state of the particle 30 calculated in step SA3 is set as the current state.

The processes from step SA3 to step SA7 are repeatedly performed until the analysis is finished (step SA8). In a case where the analysis is finished, a simulation result is output (step SA9).

Next, with reference to FIGS. 3A to 3C, a description will be made of the pressure control in step SA5 in FIG. 2.

Figure 3A:
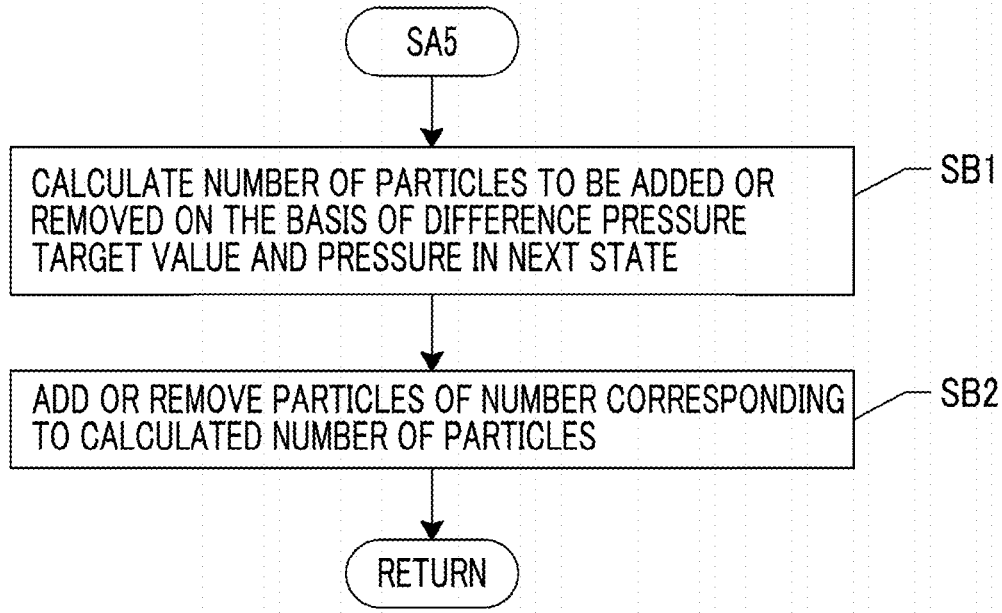
FIG. 3A is a flowchart illustrating details of step SA5 in FIG. 2.

FIG. 3A is a flowchart illustrating details of step SA5. The number of particles 30 to be added to or removed from the first heat bath 11 and the second heat bath 12 is calculated on the basis of a comparison result between the pressure (the pressure in the next state of the particle 30) calculated in step SA4 and the pressure target value (step SB1).

If a total number of particles 30 in the first heat bath 11 in the next state calculated in step SA3 is indicated by N, the pressure in the first heat bath 11 in the next state is indicated by Pn, and the pressure target value is indicated by Pt, the number dN of particles to be added is calculated according to the following equation.

$$dN = \mathrm{floor}\left(\frac{Pt - Pn}{Pn} \times N\right) \quad (1)$$

Here, the floor function is a function for producing an integer by truncating decimal places. Instead of truncating decimal places, an integer may be produced by rounding up decimal places, and may be produced by rounding off the first decimal place.

Particles of the number corresponding to the calculated number dN are added to or removed from the first heat bath 11 (step SB2). Specifically, in a case where the number dN is positive, the particles 30 are added, in a case where the number dN is negative, the particles 30 are removed, and, in a case where the number dN is 0, the particles 30 are neither added nor removed. The particles 30 are also added to or removed from the second heat bath 12 in the same manner as in the first heat bath 11.

Figure 3B:
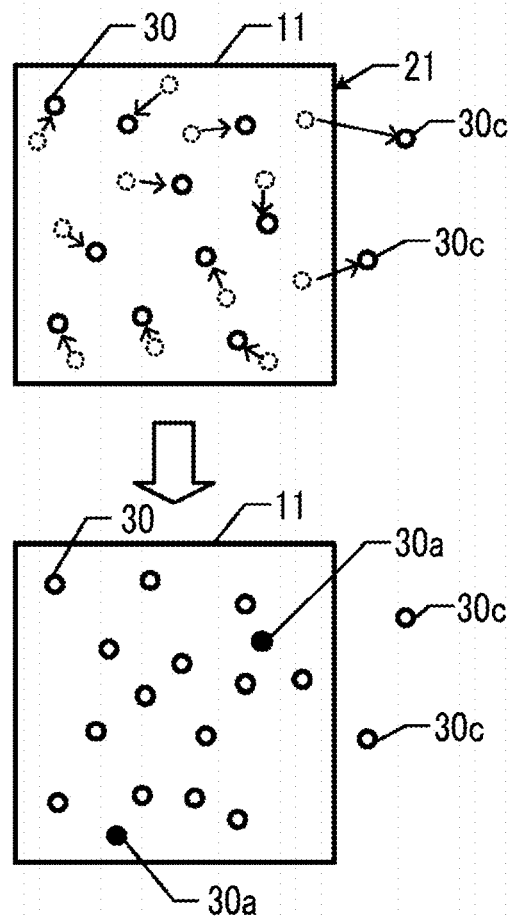
FIG. 3B is a schematic diagram illustrating a state in which particles are added in a case where the number dN is positive.

FIG. 3B is a schematic diagram illustrating a state in which the particles 30 are added in a case where the number dN is positive. In FIG. 3B, a position of the particle 30 at the present time is indicated by a dashed line, and a position of the particle 30 in the next state is indicated by a solid line. In a case where the present time transitions to the next state, two particles 30c flow to the outside from the first heat bath 11 through the inflow/outflow interface 21. In the next state, the number of particles in the first heat bath 11 is reduced, and thus a pressure therein is reduced. Thus, a relationship of Pt>Pn is established, and the number dN becomes positive. As an example, in a case where dN=2, two particles 30a are added to the first heat bath 11 as illustrated in the lower part in FIG. 3B.

If a distance between the added new particle 30a and the particle 30 which is already present is too short, large repulsive force due to the Lennard-Jones potential act on both of the particles. As a result, the particles are rapidly accelerated in the next time step, and there is a probability that calculation may fail. In a case where repulsive force acting between the added new particle 30a and the particle 30 which is already present exceeds a predetermined allowable upper limit value, the added new particles 30a are redisposed.

FIG. 3C is a schematic diagram illustrating a state in which the particles 30 are removed in a case where the number dN is negative. In FIG. 3C, a position of the particle 30 at the present time is indicated by a dashed line, and a position of the particle 30 in the next state is indicated by a solid line. In a case where the present time transitions to the next state, two particles 30d flow into the second heat bath 12 through the inflow/outflow interface 22. In the next state, the number of particles in the second heat bath 12 increases, and thus a pressure therein increases. Thus, a relationship of Pt<Pn is established, and the number dN becomes negative. As an example, in a case where dN=2, two particles 30b are removed from the second heat bath 12 as illustrated in the lower part in FIG. 3C.

Next, a description will be made of excellent effects of the simulation method according to the embodiment.

Since the first heat bath 11 and the second heat bath 12 are respectively connected to the inflow/outflow interfaces 21 and 22 of the analysis region 20, and temperature control and pressure control are performed on the first heat bath 11 and the second heat bath 12, temperatures and pressures at the inflow/outflow interfaces 21 and 22 of the analysis region 20 can be controlled.

In the embodiment, a particle is added or removed such that a pressure is close to a target value according to a change in the pressure due to a change in the number of particles. Thus, if a predetermined time elapses from starting of analysis, an equilibrium state occurs in which pressures and the number of particles in the first heat bath 11 and the second heat bath 12 are substantially maintained at target values. Consequently, a pressure can be maintained at a constant target value. Pressures in the first heat bath 11 and the second heat bath 12 are controlled, and thus pressures at the inflow/outflow interfaces 21 and 22 of the analysis region 20 can be maintained at target values.

Next, with reference to FIG. 4, a description will be made of a simulation method according to a modification example of the embodiment. In the embodiment, in a case where a pressure in the first heat bath 11 is reduced, the new particle 30a (FIG. 3B) is added at any position in the first heat bath 11, and, in a case where repulsive force acting between the added particle 30a and the existing particle 30 is too large, the particle is redisposed. In the present modification example, a probability of the occurrence of a situation in which repulsive force acting between the added particle 30a and the existing particle 30 is too large is reduced.

FIG. 4 is a schematic diagram of the first heat bath 11 for explaining the present modification example. In the present modification example, the first heat bath 11 is divided into a plurality of cells 40 having the same volume. The cells 40 are virtually separate, and boundaries of the cells 40 do not influence movement of the particles 30. FIG. 4 illustrates the cells 40 in a certain section of the first heat bath 11. Actually, the first heat bath 11 is three-dimensionally divided in the transverse direction, the longitudinal direction, and the height direction. The number n of particles 30 in the next state is calculated for each of the cells 40 before step SB2 (FIG. 3A). As an example, FIG. 4 illustrates an example in which the number n of particles of the upper right cell 40 is 2, the number n of particles of the uppermost cell 40 in the central column is 3, and the number of particles of other cells 40 is 4.

In step SB2, a new particle 30 is preferentially added to the cell 40 having a relatively small number of particles. For example, first, a new particle 30e is added to the cell 40 (the upper right cell 40 in FIG. 4) having the smallest number of particles. The number of particles of the cell 40 to which the particle is add is increased by 1. Next, a new particle 30f is added to the cell 40 (the upper right cell or the uppermost cell 40 in the central column in FIG. 4) having the smallest number of particles at that time. This process is repeatedly performed until particles of the number dN to be added are added.

In the present modification example, since the new particle 30a is added to a location having a relatively low particle density in the first heat bath 11, it is possible to reduce a probability of the occurrence of a situation in which repulsive force acting between the added particle 30a and the existing particle 30 is too large.

In a case where the particle 30 in the second heat bath 12 is removed, the particle 30b (FIG. 3C) to be removed from the cell 40 having a relatively large number of particles may be extracted.

In the embodiment, the first heat bath 11 is connected to the inflow/outflow interface 21 on the upstream side of the flow field, and the second heat bath 12 is connected to the inflow/outflow interface 22 on the downstream side of the flow field. Whether the first heat bath 11 or the second heat bath 12 is on the upstream side is determined according to boundary conditions for the inflow/outflow interfaces 21 and 22, and thus the first heat bath 11 and the second heat bath 12 are not required to be handled separately in simulation. Depending on an analysis time step, there may be a case where a particle is removed from the first heat bath 11 connected to the upstream side, and a new particle is added to the second heat bath 12 connected to the downstream side, according to movement for a short period of time.

In the embodiment, pressure control is performed for each time step, but the pressure control is not necessarily required to be performed in all time steps. For example, the pressure control may be performed at an interval of a plurality of predetermined time steps. Alternatively, the pressure control may be performed in a case where a difference between a pressure in each of the first heat bath 11 and the second heat bath 12 and a pressure target value exceeds a predetermined allowable upper limit value.

Next, with reference to FIGS. 5 to 6B, a description will be made of results of performing simulation on the first heat bath 11.

Figure 5:
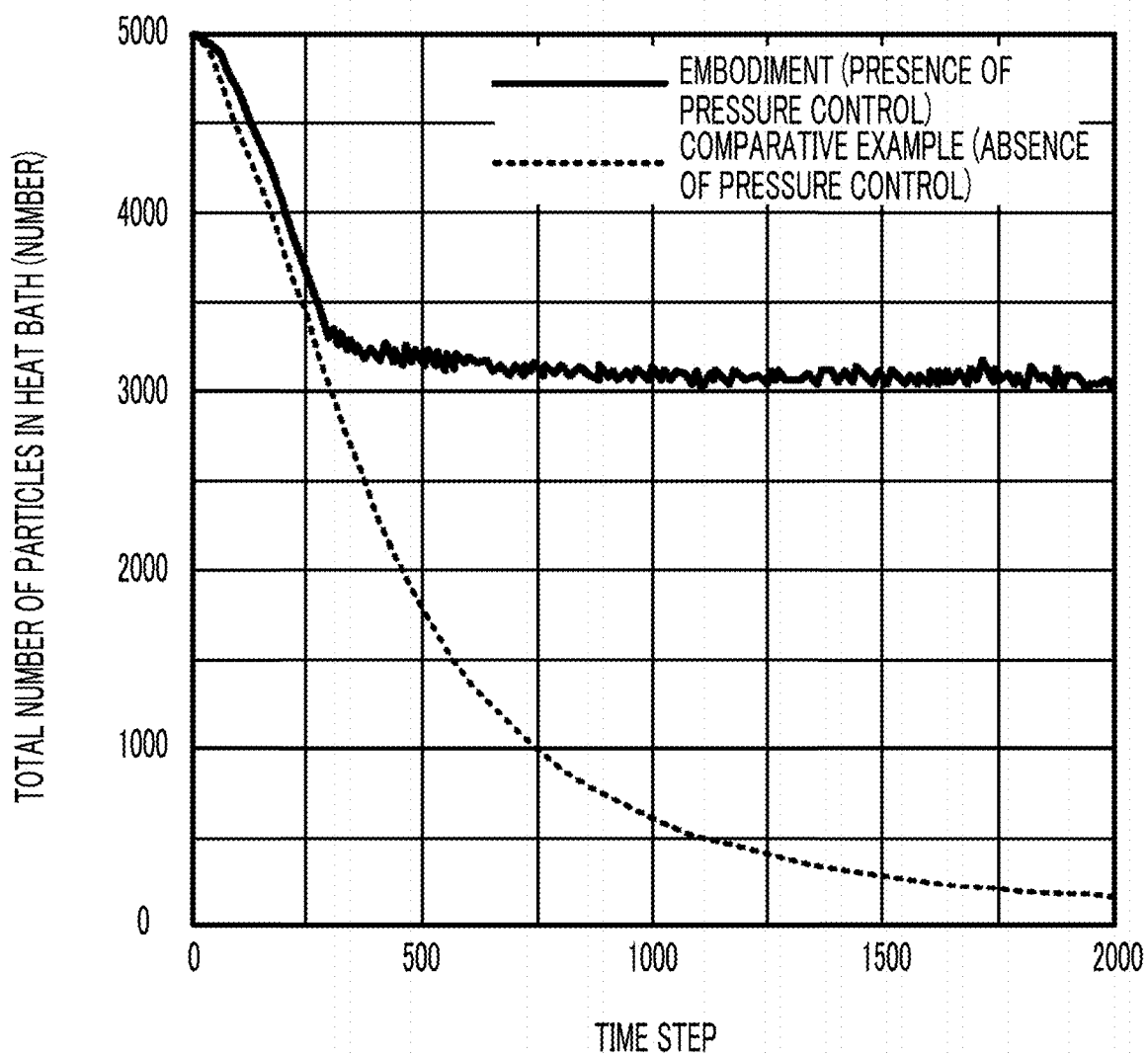
FIG. 5 is a graph illustrating a temporal change of a total number of particles in the first heat bath.

FIG. 5 is a graph illustrating a temporal change of a total number of particles in the first heat bath 11. A transverse axis expresses a time step, and a longitudinal axis expresses a total number of particles. In the graph in FIG. 5, a solid line indicates a result of applying the simulation method according to the embodiment of performing pressure control, and a dashed line indicates a result of applying a simulation method according to a comparative example of not performing pressure control.

In the comparative example of not performing pressure control, a particle flows out of the first heat bath 11, and thus a total number of particles is reduced with the passage of time. In the embodiment of performing pressure control, a total number of particles is reduced with the passage of time until the number of time steps reaches about 300, but, thereafter, a total number of particles is maintained to be substantially constant. The reason why a total number of particles is initially reduced is that an initial value of a pressure in the heat bath is set to be higher than a pressure target value. If a time step progresses to about 300, the pressure in the heat bath is almost the same as the target value. In the embodiment, a new particle is added such that the pressure is maintained at the target value, and thus a total number of particles is substantially constant.

Figure 6A:
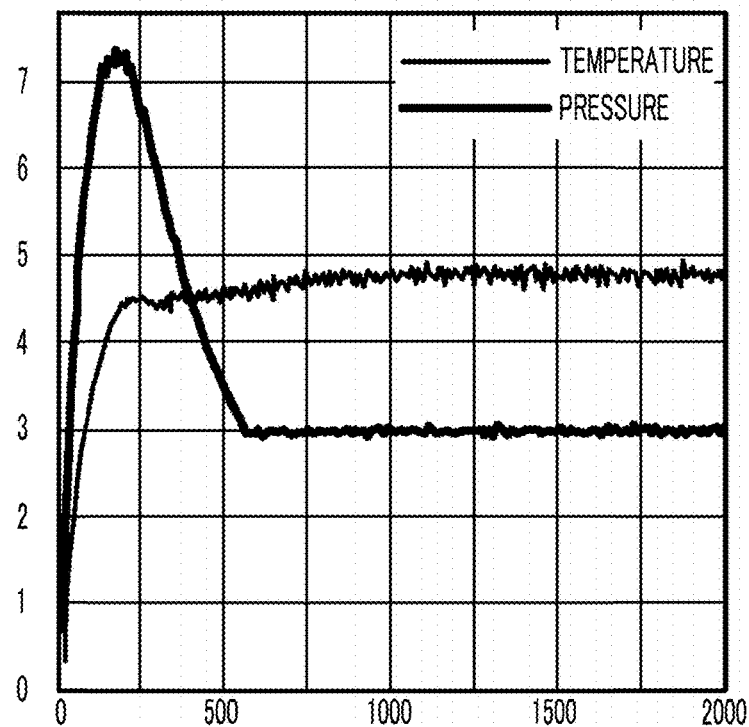
FIG. 6A is a graph illustrating temporal changes of a temperature and a pressure in the heat bath in a case where the simulation method according to the embodiment is applied.
Figure 6B:
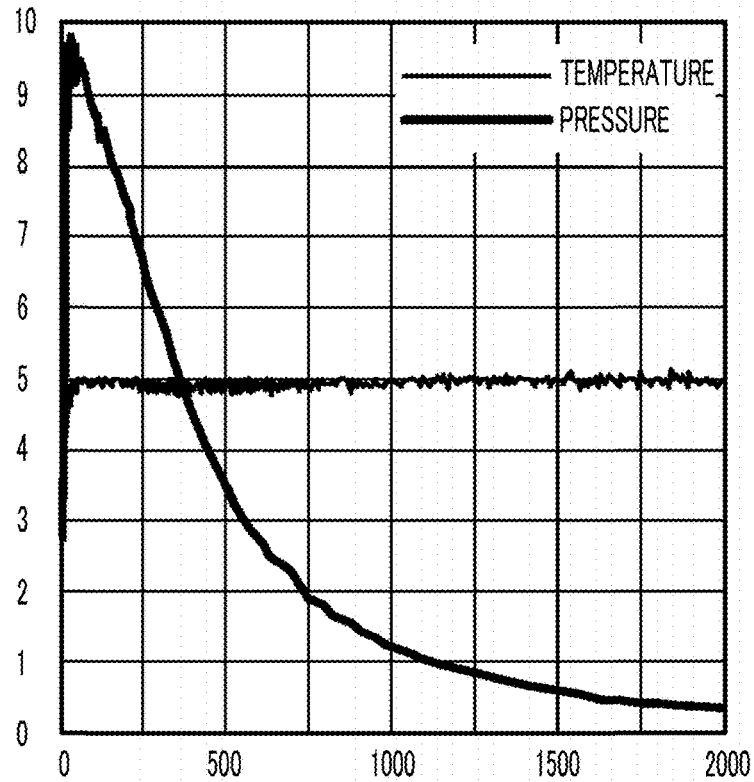
FIG. 6B is a graph illustrating temporal changes of a temperature and a pressure in the heat bath in a case where a simulation method according to a comparative example in which pressure control is not performed is applied.

FIG. 6A is a graph illustrating temporal changes of a temperature and a pressure in the heat bath in a case where the simulation method according to the embodiment is applied. FIG. 6B is a graph illustrating temporal changes of a temperature and a pressure in the heat bath in a case where the simulation method according to the comparative example of not performing pressure control is applied. In FIGS. 6A and 6B, a transverse axis expresses a time step, and a longitudinal axis therein expresses a temperature and a pressure in arbitrary unit. In the graphs, a thick solid line and a thin solid line respectively indicate temporal changes of a pressure and a temperature. In both of the embodiment and the comparative example, a temperature is controlled to be maintained at a target value according to a temperature control algorithm.

In the embodiment (FIG. 6A), the pressure is maintained to be substantially constant from a time point at which the number of time steps exceeds 500. In contrast, in the comparative example (FIG. 6B), the pressure is reduced with the passage of time even if the number of time steps exceeds 500. This is because a particle in the heat bath flows to the outside through the inflow/outflow interface. In the embodiment, a new particle is added to the heat bath, and thus the pressure is maintained at the target value.

In both cases of the embodiment and the comparative example, since temperature control is performed, a temperature is close to a target value with the passage of time, and then the point is substantially maintained at the target value.

Next, with reference to FIG. 7, a description will be made of a simulation apparatus executing each process of the simulation method according to the embodiment.

FIG. 7 is a block diagram illustrating the simulation apparatus according to the embodiment. The simulation apparatus is formed of a general computer, and includes a central processing unit (CPU; a processing device) 50, a memory 51, an input/output device 52, and an auxiliary storage device 53. The constituent elements are connected to each other via a bus 54.

The input/output device 52 includes pointing devices such as a keyboard and a mouse, a display, a reader/writer for removable media, a communication device, and the like. The display displays various windows required for a user to perform an operation, data, or the like. The communication device performs data communication with an external apparatus. The user performs the input/output device so as to give an instruction for the computer and to input data required in each process. A process result is output to the input/output device.

The auxiliary storage device 53 is formed of a hard disk or the like, and stores an OS of the computer, a simulation program, data or a process result required in simulation, and the like.

The memory 51 is formed of a read only memory (ROM), a random access memory (RAM), or the like. The memory 51 stores the simulation program or the like read from the auxiliary storage device 53 by the CPU 50.

The CPU 50 performs various calculations or control of the input/output device 52 and the auxiliary storage device 53 on the basis of the OS of the computer, the simulation program stored in the memory 51, and the like.

Next, a description will be made of an operation of the simulation apparatus. The CPU 50 acquires initial conditions and boundary conditions from the input/output device 52 in order to perform the process in step SA1 (FIG. 2). For example, the user operates the input/output device 52 so as to input the initial conditions and the boundary conditions. Alternatively, the CPU 50 reads the initial conditions and the boundary conditions from a removable medium. Thereafter, the CPU 50 performs the process in step SA2, and repeatedly performs the processes in steps SA3 to SA8. In step SA9, the CPU 50 displays, for example, an analysis result on the display.

The embodiment and the modification examples are only examples, partial replacement or combination of the configurations described in the embodiment and the modification examples may occur. The same advantageous effects based on the same configurations as those in the embodiment and the modification examples are not sequentially described in the embodiment and the modification examples. The present invention is not limited to the embodiment and the modification examples. For example, it is clear to a person skilled in the art that various alterations, modifications, combinations, and the like may occur.

It should be understood that the invention is not limited to the above-described embodiment, but may be modified into various forms on the basis of the spirit of the invention. Additionally, the modifications are included in the scope of the invention.

What is claimed is:

1. A simulation method comprising:
   setting, by a processing device, a flow field having a first inflow/outflow interface and a second inflow/outflow interface as a region for analyzing;
   handling, by the processing device, a fluid in the flow field as an aggregate of a plurality of particles; and
   analyzing, by the processing device, a behavior of a particle by using a molecular dynamics method,
   wherein the processing device is configured to perform a process of maintaining a first temperature and a first pressure at the first inflow/outflow interface and a second temperature and a second pressure at the second inflow/outflow interface, as boundary conditions, at target values by compensating for changes in the first temperature and the first pressure in a first heat bath and the second temperature and the second pressure in a second heat bath with the passage of time in an analysis model in which:
   the first heat bath is connected to the first inflow/outflow interface of the region for analyzing,
   the second heat bath is connected to the second inflow/outflow interface of the region for analyzing, and
   a particle is movable between the first heat bath, the second heat bath, and the region for analyzing,
   wherein, in the process of maintaining the first pressure in the first heat bath or the second pressure in the second heat bath at the target values:
   the first pressure in the first heat bath or the second pressure in the second heat bath is calculated on a basis of a number and states of the particles in the first heat bath or the second heat bath at a present time,
   the calculated first pressure in the first heat bath or the calculated second pressure in the second heat bath at the present time is compared with a pressure target value, and a number of particles to be added to or removed from the first heat bath or the second heat bath is calculated on a basis of a comparison result, and particles of the number of the particles to be added to or removed from the first heat bath or the second heat bath are added to or removed from the first heat bath or the second heat bath, and wherein, in the process of adding or removing the particles to or from the first heat bath or the second heat bath:

a number of particles in a cell is calculated for each of a plurality of cells into which a region of the first heat bath or the second heat bath is divided, a particle is added to a cell by prioritizing the cell having a relatively small number of particles, and a particle is removed from a cell by prioritizing the cell having a relatively large number of particles.

2. A simulation apparatus comprising:

an input/output device; and a processing device that:

sets a flow field having a first inflow/outflow interface and a second inflow/outflow interface as a region for analyzing, handles a fluid in the flow field as an aggregate of a plurality of particles, analyzes a behavior of a particle by using a molecular dynamics method, acquires target values of a first temperature and a second temperature, target values of a first pressure and a second pressure, and initial conditions for the first inflow/outflow interface and the second inflow/outflow interface of the region of analyzing, maintains the first temperature and the first pressure at the first inflow/outflow interface and the second temperature and the second pressure at the second inflow/outflow interface, as boundary conditions, at target values by compensating for changes in the first temperature and the first pressure in a first heat bath and the second temperature and the second pressure in a second heat bath with a passage of time in an analysis model in which the first heat bath is connected to the first inflow/outflow interface of the region of analyzing, the second heat bath is connected to the second inflow/outflow interface of the region of analyzing, and a particle is movable between the first heat bath, the second heat bath, and the region of analyzing, analyzes behaviors of particles in the region of analyzing and the first and second heat baths by using the molecular dynamics method, and outputs an analysis result from the input/output device, wherein, in the process of maintaining the first pressure in the first heat bath or the second pressure in the second heat bath at the target values, the processing device:

calculates the first pressure in the first heat bath or the second pressure in the second heat bath on a basis of the number and states of particles in the first heat bath or the second heat bath at a present time, compares the calculated first pressure in the first heat bath or the calculated second pressure in the second heat bath at the present time with a pressure target value, and calculates a number of particles to be added to or removed from the first heat bath or the second heat bath on a basis of a comparison result, and adds or removes particles of the calculated number to or from the first heat bath or the second heat bath, and wherein, in the process of adding or removing the particles to or from the first heat bath or the second heat bath, the processing device:

calculates a number of particles in a cell for each of a plurality of cells into which a region of the first heat bath or the second heat bath is divided, adds a particle to a cell by prioritizing the cell having a relatively small number of particles, and removes a particle from a cell by prioritizing the cell having a relatively large number of particles.

* * * * *